United States Patent
Brassart et al.

(10) Patent No.: US 10,758,555 B2
(45) Date of Patent: Sep. 1, 2020

(54) COMPOSITIONS FOR PREVENTING OR TREATING ALLERGIES IN INFANTS FROM OR FED BY NON SECRETOR MOTHERS BY PROVIDING FUCOSYLATED-OLIGOSACCHARIDES IN PARTICULAR AMONG INFANTS AT RISK OR BORN BY C-SECTION

(71) Applicant: NESTEC S.A., Vevey (CH)

(72) Inventors: Dominique Brassart, Chavannes-pres-renens (CH); Clemens Kunz, Wettenberg (DE); Norbert Sprenger, Savigny (CH)

(73) Assignee: Societe des Produits Nestle S.A., Vevey (CH)

( * ) Notice: Subject to any disclaimer, the term of this patent is extended or adjusted under 35 U.S.C. 154(b) by 11 days.

(21) Appl. No.: 15/036,911

(22) PCT Filed: Nov. 4, 2014

(86) PCT No.: PCT/EP2014/073623
§ 371 (c)(1),
(2) Date: May 16, 2016

(87) PCT Pub. No.: WO2015/071131
PCT Pub. Date: May 21, 2015

(65) Prior Publication Data
US 2016/0296543 A1    Oct. 13, 2016

(30) Foreign Application Priority Data
Nov. 15, 2013 (EP) ..................................... 13193038

(51) Int. Cl.
| | | |
|---|---|---|
| A61K 31/702 | (2006.01) | |
| A23L 33/00 | (2016.01) | |
| A23L 33/10 | (2016.01) | |
| A61P 37/00 | (2006.01) | |
| A23L 33/125 | (2016.01) | |

(52) U.S. Cl.
CPC ............ *A61K 31/702* (2013.01); *A23L 33/10* (2016.08); *A23L 33/125* (2016.08); *A23L 33/40* (2016.08); *A61P 37/00* (2018.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 7,112,322 B2* | 9/2006 | Isolauri | ................ | A61K 35/745 424/93.45 |
| 8,771,674 B2* | 7/2014 | Sprenger | .............. | A61K 31/702 424/93.4 |
| 9,161,563 B2* | 10/2015 | Sprenger | ................ | A23L 1/296 |
| 9,763,465 B2* | 9/2017 | Sprenger | ................ | A23L 33/40 |
| 10,357,506 B2* | 7/2019 | Sprenger | .............. | A61K 31/702 |
| 2013/0243797 A1* | 9/2013 | Sprenger | .............. | A61K 31/702 424/184.1 |
| 2013/0251844 A1* | 9/2013 | Sprenger | ................ | A23L 1/296 426/2 |
| 2016/0287618 A1* | 10/2016 | Sprenger | ................ | A61K 45/06 |

FOREIGN PATENT DOCUMENTS

| | | |
|---|---|---|
| CN | 1107658 A | 9/1995 |
| CN | 1494509 A | 5/2004 |
| RU | 2426549 C2 | 8/2011 |
| RU | 2456008 C2 | 7/2012 |
| WO | 2011008086 | 1/2011 |
| WO | 2011090926 | 7/2011 |
| WO | 2011136648 | 11/2011 |
| WO | 2012069416 | 5/2012 |
| WO | 2012076321 A1 | 6/2012 |
| WO | 2012092154 A1 | 7/2012 |
| WO | 2012092159 A1 | 7/2012 |

OTHER PUBLICATIONS

U.S. Appl. No. 15/554,738, filed Aug. 2017, Sprenger, Norbert.*
U.S. Appl. No. 15/555,168, filed Sep. 2017, Sprenger, Norbert.*
U.S. Appl. No. 15/554,621, filed Aug. 2017, Sprenger, Norbert.*
U.S. Appl. No. 15/554,369, filed Aug. 2017, Sprenger, Norbert.*
Merriam-Webster's Collegiate Dictionary, published 1998 by Merriam-Webster, Incorporated, p. 924 (Year: 1998).*
Bode, Lars "Human milk oligosaccharides: Every baby needs a sugar mama" Glycobiology (2012) vol. 22 No. 9, pp. 1147-1162 (Year: 2012).*
Thurl et al., "Variation of human milk oligosaccharides in relation to milk groups and lactational periods" British Journal of Nutrition, vol. 104 pp. 1261-1271 (Year: 2010).*
Morrow et al., "Human Milk Oligosaccharides Are Associated With Protection Against Diarrhea in Breast-Fed Infants" Journal of Pediatrics pp. 297-303 (Year: 2004).*
Ereny et al., "Variability of Human Milk Neutral Oligosaccharides in a Diverse Population" Journal of Pediatric Gastroenterology and Nutrition vol. 30 No. 2 pp. 181-192 (Year: 2000).*
Penders et al., "Gut microbiota composition and development of atopic manifestations in infancy: the KOALA Birth Cohort Study" Gut vol. 56 pp. 661-667 (Year: 2007).*
McGuire et al., "Infection in the preterm infant" British Medical Journal vol. 329 pp. 1277-1280 (Year: 2004).*
Pullan et al., "Wheezing, asthma, and pulmonary dysfunction 10 years after infection with respiratory syncytial virus in infancy" British Medical Journal vol. 284 pp. 1665-1669 (Year: 1982).*
Korpella et al., "Fucosylated oligosaccharides in mother's milk alleviate the effects of cesarean birth on infant gut microbiota" Scientific reports vol. 8 pp. 1-7 (Year: 2018).*

(Continued)

*Primary Examiner* — Eric Olson
(74) *Attorney, Agent, or Firm* — K&L Gates LLP

(57) ABSTRACT

The present invention relates to a composition comprising at least one fucosylated oligosaccharide, for use in preventing allergies and/or treating allergies and/or reducing the occurrence or the risk of allergies in an infant or a young child born from a mother deficient in at least one fucosylated oligosaccharide(s) or fed with a mother's milk deficient in at least one fucosylated oligosaccharide(s). The use of said composition in infant formula, milk fortifier or children's food is foreseen.

11 Claims, 4 Drawing Sheets

(56) References Cited

OTHER PUBLICATIONS

Thurl et al. "Variation of human milk oligosaccharides in relation to milk groups and lactational periods" British Journal of Nutrition, 2010, vol. 104, pp. 1261-1271.
Sjogren et al. "Neutral oligosaccharides in colostrum in relation to maternal allergy and allergy development in children up to 18 months of age" Pediatric Allergy and Immunology, 2007, vol. 18, pp. 20-26.
Totten et al. "Comprehensive Profiles of Human Milk Oligosaccharides Yield Highly Sensitive and Specific Markers for Determining Secretor Status in Lactating Mothers" Journal of Proteome Research, 2012, vol. 11, pp. 6124-6133.
Morrow et al., "Fucosyltransferase 2 non-secretor and low secretor status predicts severe outcomes in premature infants", J. Pediatr., May 2011, vol. 158, No. 5, pp. 745-751.
Russian Office Action for Application No. 2016123459, dated Jul. 9, 2018.
Yin, "Book for Allergic Diseases", Zhongyuan Farmers Press, 1st Edition, Mar. 31, 2013, 16 pages.
China Patent Office Communication for Application No. 201480057223.X, dated Jun. 22, 2020, 14 pages.

* cited by examiner

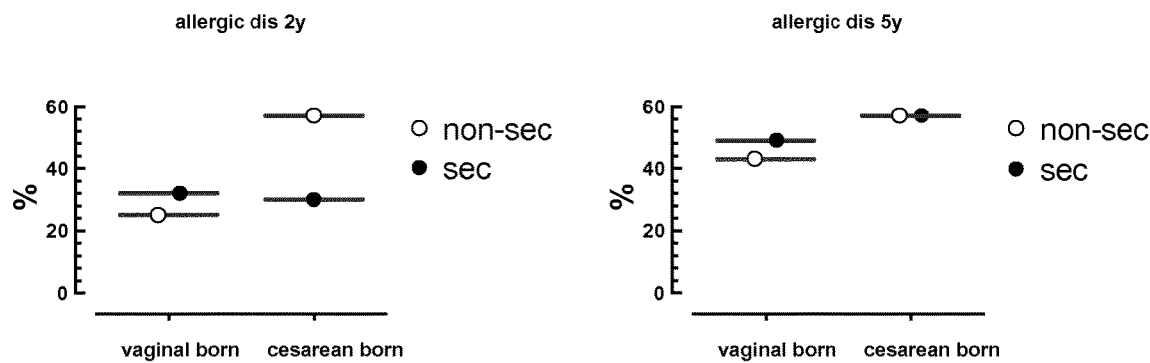
*Figure 1.* Plotted are percent of infants who developed an allergic disease up to 2 years (left hand side) and up to 5 years (right hand side) separated into vaginal and cesarean born infants (x-axis) and whether they consumed secretor milk (sec) or non-secretor milk (non-sec) from their mothers in the first months of life.

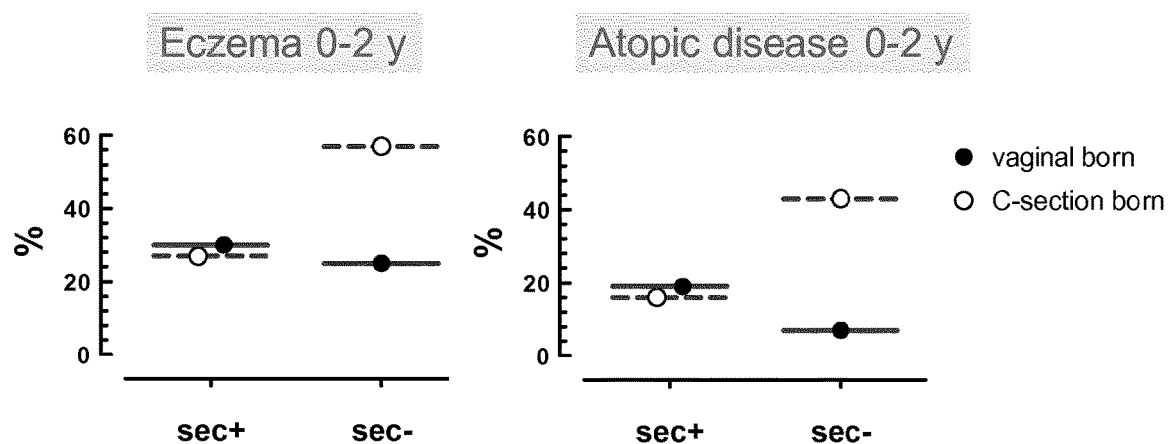
*Figure 2.* Plotted are percent of infants who developed eczema or an atopic disease up to 2 years separated into vaginal and cesarean born infants and whether they consumed secretor milk (sec+) or non-secretor milk (sec-) from their mothers in the first months of life.

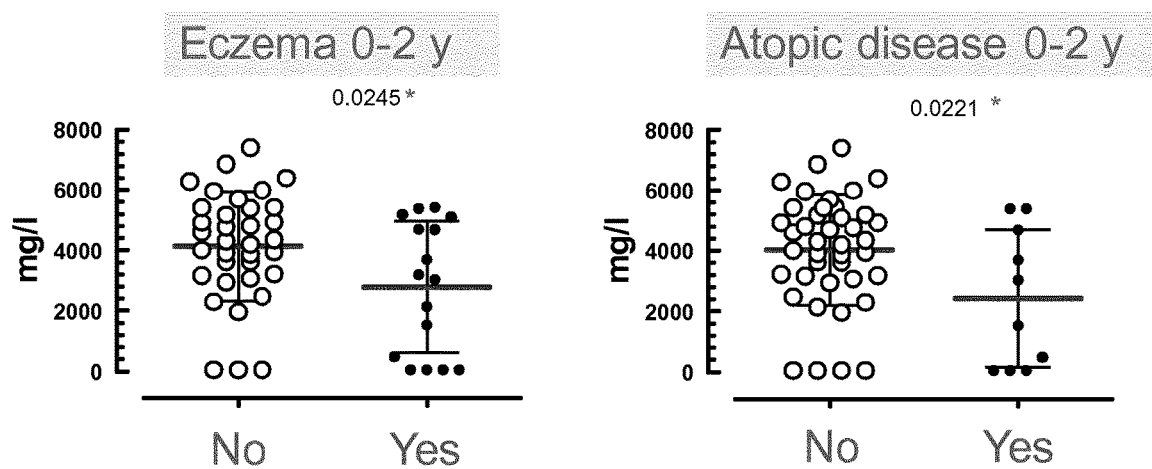
*Figure 3.* Plotted are amounts of 2FL in early milk consumed by infants who developed eczema (yes) or not (No) and who developed an atopic disease (yes) or not (No) up to 2 years. Mean and STD with statistical significance are shown.

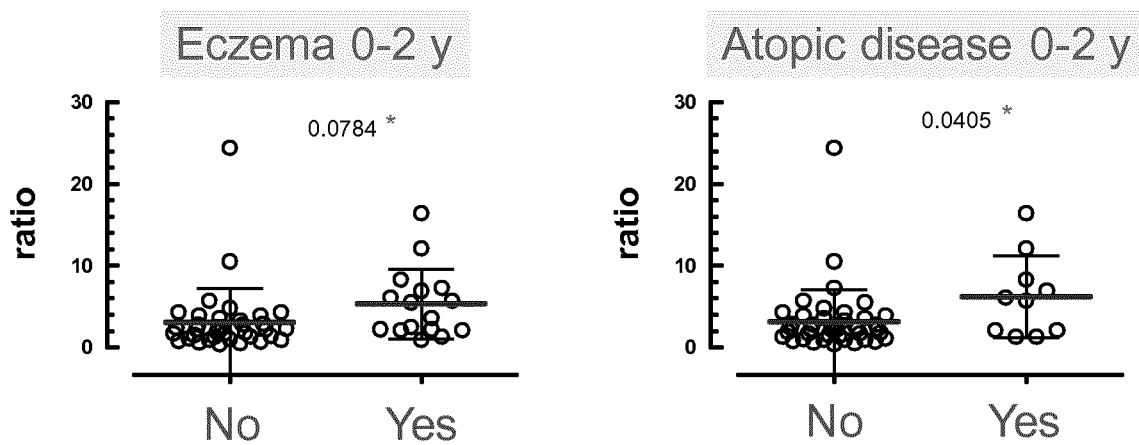
*Figure 4.* Plotted are ratios of LNT/LNnT in early milk consumed by infants who developed eczema (yes) or not (No) and who developed an atopic disease (yes) or not (No) up to 2 years. Mean and STD with statistical significance are shown.

COMPOSITIONS FOR PREVENTING OR TREATING ALLERGIES IN INFANTS FROM OR FED BY NON SECRETOR MOTHERS BY PROVIDING FUCOSYLATED-OLIGOSACCHARIDES IN PARTICULAR AMONG INFANTS AT RISK OR BORN BY C-SECTION

CROSS REFERENCE TO RELATED APPLICATIONS

The present application is a National Stage of International Application No. PCT/EP2014/073623, filed on Nov. 4, 2014, which claims priority to European Patent Application No. 13193038.0, filed Nov. 15, 2013, the entire contents of which are being incorporated herein by reference.

FIELD OF THE INVENTION

This invention relates to compositions for use in preventing and/or treating allergies in subgroups of infants having high risks of allergies.

BACKGROUND OF THE INVENTION

For the prevention and/or treatment of allergies in subgroups of infants with high risk for allergies, different routes have been explored such as the use of probiotics or the use of oligosaccharides, and especially human milk oligosaccharides. Human milk oligosaccharides (HMOs) are, collectively, the third largest solid constituents in human milk, after lactose and fat. HMOs usually consist of lactose at the reducing end with a carbohydrate core that often contains a fucose or a sialic acid at the non-reducing end. There are approximately one hundred milk oligosaccharides that have been isolated and characterized in human milk, however this represents only a very small portion of the total number remaining to be characterized. Mother's milk is recommended for all infants. However, in some cases breast feeding is inadequate or unsuccessful for medical reasons or the mother chooses not to breast feed. Infant formulae have been developed for these situations. Fortifiers have also been developed to enrich mother's milk or infant formula with specific ingredients.

Several compositions have therefore been developed using HMO ingredients, such as fucosylated oligosaccharides, lacto-N-tetraose, lacto-N-neotetraose, or sialylated oligosaccharides, and for different purposes.

For example WO2005055944 from Children's hospital medical center describes a pharmaceutical composition comprising a molecule comprising a fucose group in an alpha-2 linkage, an alpha-3 linkage or an alpha-4 linkage to a galactose group and a pharmaceutically acceptable carrier. Various molecules are described such as 2'-fucosyllactose. This application is quite general since several infections can be prevented or treated, including respiratory or enteric infections, and there is a large target of patients (infants, children or adults).

Further documents specifically focus on various associations of HMOs with either a probiotic strain or with other specific components.

For example WO2009/077352 from Nestec SA relates to a composition suitable in the prevention of opportunistic infections comprising a particular synergetic association of a probiotic *Bifidobacterium* with a fucosylated oligosaccharide. Respiratory tracts infections are cited amongst the opportunistic infections that may be prevented. This invention especially targets immune-compromised individuals such as preterm and neonatal infants, older children or even adults with an immune system which is not fully effective as a result of an existing condition or illness (e.g. HIV) or as a result of therapy for an existing condition e.g. Crohn's disease or rheumatoid arthritis or chemo-therapy for the treatment of cancer).

WO2009/112361 from Nestec SA relates to another composition suitable in the prevention of opportunistic infections comprising a particular synergetic association of a N-acetyl-lactosamine and/or an oligosaccharide containing N-acetyl-lactosamine with a probiotic *Lactobacillus* sp. Several conditions are cited such as pathogenic infections of the upper respiratory tract.

WO2012/092154 from Abbott refers to methods of using HMOs for improving airway respiratory health of infants, toddlers and children. However a wide list of HMOs is indicated in this application as well as several combinations of different HMOs. It is claimed that the composition seems to be efficient when HMOs are present with carotenoid.

WO2012076321 from Nestec SA discloses specific oligosaccharides for treating skin disease in general populations.

WO2011/136648 from Nutricia is focused on the use of a composition comprising HMOs such as 2-fucosylated oligosaccharides for the preparation of a nutritional composition for feeding an infant, said infant having Lewis blood type Le(a−/b+) or Le(a−/b−) and/or Lewis blood type Le(x−/y+) or Le(x−/y−). However this application does not refer to the prevention and/or treatment of allergies.

None of the previous work is therefore focused on the health benefits related to allergy in high risk subjects. These high risk subjects represent a sub-group of subjects of a higher concern and who require a higher care than the other infants since they will be more prone to get such diseases and the associated complications.

There is therefore a need for these infants or young child at risk to develop an efficient specific composition that will allow preventing, reducing and/or treating allergies.

There is a need to deliver specific means of delivering such anti-allergy health benefit, more specifically in high risk subjects. There is s further need to deliver such health benefit in a manner that is particularly suitable for young subjects such as infants or young children, in a manner that does not involve a classical pharmaceutical intervention as these infants or young child are particularly fragile. There is a need to deliver such health benefits in at risk subjects in a manner that does not induce side effects and/or in a manner that is easy to deliver, and well accepted by the parents or health care practitioners.

There is a need to deliver such benefits in a manner that does keep the cost of such delivery reasonable and affordable by most.

Overall there is a need to deliver the most appropriate positive health effects to the specific sub-populations in needs, without unnecessarily targeting broad and large populations.

SUMMARY OF THE INVENTION

The present inventors were able to identify infants having higher risks to have allergic manifestations. Such infant are infants born from a mother deficient in at least one fucosylated oligosaccharide(s) or fed with a mother's milk that is deficient in at least one fucosylated oligosaccharide(s). More particularly at risk are infants having additional risk factors:

infants from with a family history of allergy, infants born by C-section and/or infants having siblings.

The present inventors have found that a composition comprising at least one fucosylated oligosaccharide can advantageously be used to provide an anti-allergic effect in said infants or young children at risk.

Accordingly, the present invention provides a composition comprising at least one fucosylated oligosaccharide, for use in preventing, reducing and/or treating allergies in particular sub-populations of infants or young children.

FIGURES

FIG. 1 shows the frequency of occurrence of allergic diseases at 2 years and at 5 years in a population of infants vaginally born or born by caesarean section, and having consumed secretor's mother milk or non-secretor's mother's milk in the first months of life.

FIG. 2 shows the frequency of occurrence of eczema and atopic disease at 2 years and at 5 years in a population of infants vaginally born or born by caesarean section, and having consumed secretor's mother milk or non-secretor's mother's milk in the first months of life.

FIG. 3 shows the relationship between the amount of 2FL present in the mother's milk consumed in the first months of life of infants and the occurrence (yes/no) of eczema (left panel) or atopic disease (right panel) during the first 2 years of life.

FIG. 4 shows the relationship between the ratio LNT/LNnT present in the mother's milk consumed in the first months of life of infants and the occurrence (yes/no) of eczema (left panel) or atopic disease (right panel) during the first 2 years of life.

DETAILED DESCRIPTION OF THE INVENTION

Definitions

As used herein, the following terms have the following meanings.

The term "infant" means a child under the age of 12 months.

The expression "young child" means a child aged between one and three years, also called toddler.

An "infant or young child born by C-section" means an infant which was delivered by caesarean section. It means that the infant was not vaginally delivered.

A "preterm" or "premature" means an infant or young child that was not born at term. Generally it refers to an infant born prior 36 weeks of gestation.

The expression "nutritional composition" means a composition which nourishes a subject. This nutritional composition is usually to be taken enterally, orally, parenterally or intravenously, and it usually includes a lipid or fat source and a protein source.

The expression "hypoallergenic nutritional composition" means a nutritional composition which is unlikely to cause allergic reactions.

The expression "synthetic composition" means a mixture obtained by chemical and/or biological means, which can be chemically identical to the mixture naturally occurring in mammalian milks.

The expression "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae).

The expression "starter infant formula" means a foodstuff intended for particular nutritional use by infants during the first four months of life.

The expression "follow-on formula" means a foodstuff intended for particular nutritional use by infants aged over four months and constituting the principal liquid element in the progressively diversified diet of this category of person.

The expression "baby food" means a foodstuff intended for particular nutritional use by infants during the first years of life.

The expression "infant cereal composition" means a foodstuff intended for particular nutritional use by infants during the first years of life.

The expression "fortifier" refers to liquid or solid nutritional compositions suitable for mixing with breast milk or infant formula.

The term "weaning period" means the period during which the mother's milk is substituted by other food in the diet of an infant.

The "mother's milk" should be understood as the breast milk or colostrum of the mother.

In the present invention the "infant(s) or young child at risk" represent subjects having higher risk of allergies than usual (i.e. than the risk of the average population), especially higher risks of skin allergic manifestations. The risk can manifest itself by a high frequency of occurrence of allergic episodes (such as allergic rhinitis, skin rash, Iatopic dermatitis etc. . . . ) during the first 6 months, 1 year, 2 years or 5 years of life. It can also include the long term risk of developing such allergies, relating to occurrence of allergic episodes after the age of 3, 5, 10, 15 or 20 years.

The infant or young child at risk according to the invention is a subject fulfilling at least one of the following criteria:
  i) the subject is born from a mother deficient in deficient in at least one fucosylated oligosaccharide(s) or is fed with a mother's milk deficient in at least one fucosylated oligosaccharide(s)
  ii) the subject has at least one sibling
  iii) the subject was born by C-section
  iv) the subject has a family history of allergy The present invention more specifically relates to infants particularly at risk because they fulfil the criteria (i) and optionally any other risk criteria such as (ii), (iii) and/or (iv).

Family History of Allergy:

A subject is considered to have a family history of allergy when at least one of his/her parent is allergic and/or experiences recurring allergic manifestations. It is understood that children with a family history of allergy are more susceptible to be or to become allergic themselves.

Allergies, Eczema, Atopic Dermatitis:

Allergies occur at any period of the subject life, however allergic manifestations occurring within the first 2 years or first 5 years of the life of the subject are of particular interest for the present invention. The prevention of allergies however can be a long term prevention, i.e. the reduction of occurrence or avoidance of allergic manifestations at any age, later in life. In one embodiment the composition of the invention has an "anti-allergic" effect during the first 2 years of the life of the subject, or during the first 5 years of the life of the subject. In one embodiment the "anti-allergic" effect is seen long term, for example during the first 10, 15 or 20 years of the life of the subject. The "anti-allergic" effect can encompass the prevention of allergies, the treatment of allergies, the reduction of the occurrence or of the risk of allergies, or any combination thereof.

Overall "allergies" can cause particular immune manifestations, inflammatory manifestations, respiratory manifestations (e.g. asthma, allergic rhinitis) or skin manifestations that are all well documented in the art.

Atopic dermatitis is a chronic itchy skin disease that is common in children but may occur at any age. It is also known as eczema or atopic eczema. There is a strong association between food allergy and atopic dermatitis in the age group of young children, and food allergies are often suspected in children with atopic dermatitis.

Atopic dermatitis usually occurs in people who have an atopic tendency. This means they may develop any or all of three closely linked conditions: atopic dermatitis, asthma and hay fever (allergic rhinitis).

A phenomenon of atopic dermatitis occurs as follows. Patches of sensitive skin flare up in a rash in response to certain triggers. These triggers vary from person to person. In the case of infants and young children, the list of common triggers to watch for includes cow's milk and other possible ingredients of infant formula such as wheat or soy. Atopic dermatitis can become a vicious cycle. Something irritates the child skin, making it red and inflamed. It itches, the child scratches it, and the skin becomes more inflamed. The outer protective layer of the skin is lost, and the affected area becomes even more sensitive to irritants and dries out easily. The infant continues to be exposed to whatever it was that triggered these episodes in the first place. The rash develops further and the cycle perpetuates itself.

There is no known single cause for atopic dermatitis. It probably reflects more than one condition. There are many theories regarding the underlying mechanisms. Current research is investigating the role of filaggrin gene mutations, defects in skin cells (keratinocytes), the immune system, skin surface microbes (bacteria, viruses and yeasts), and many other factors.

All skin conditions and skin diseases can affect the general population or the population of persons at risk of allergies or the population of allergic (hence sick) persons.

Such skin conditions and skin diseases, and in particular atopic dermatitis, are of particular importance for infants, babies or children as they have a sensitive skin that undergoes an intense growth and phases of multiplication, rendering it even more susceptible to skin diseases. The population of infants without history of allergies in their family, and who become allergic, is increasing.

WO20112076321A1 (Norbert Sprenger/Nestec SA) describes the use of particular oligosaccharides for treating skin diseases and/or atopic dermatitis in a general population.

"Deficient in at Least One Fucosylated Oligosaccharide(s)":

By the expression "deficient in at least one fucosylated oligosaccharide(s)", it is meant the mother of the infant does not express or express low levels of fucosylated oligosaccharides (or at least one of them), preferably fucosylated oligosaccharides comprising a 2'-fucosyl-epitope (also called 2-fucosylated oligosaccharides), most preferably 2FL.

Such expression is generally recognized by the absence or presence at low levels of said fucosylated oligosaccharides in the mother's milk or mother's colostrums. Alternatively such expression is recognized by genetic analysis, or measurements in other body fluids.

In one embodiment the mother's milk that lacks, is depleted of or is poor in fucosylated oligosaccharides (or at least one of them) and especially in fucosylated oligosaccharides comprising a 2'-fucosyl-epitope (also called 2-fucosylated oligosaccharides), e.g. 2FL. The milk may contain no (or almost no) fucosylated oligosaccharides, or a low amount of fucosylated oligosaccharides such as an amount which represent less than 50%, or less than 40%, or less than 35%, or less than 30%, or less than 25%, or less than 20%, or less than 15%, or less than 10%, or less than 5%, or less than 3%, or less than 2% of the mean (or average) amount that is generally found in the breast mother's milk.

In one embodiment the mother's milk or the mother's milk fed to the infant is fully depleted in at least one fucosylated oligosaccharide, preferably in fucosylated oligosaccharides comprising a 2'-fucosyl-epitope. (also called 2'-fucosylated oligosaccharides), more preferably in 2FL. Fully depleted mean that the level of oligosaccharide is not detectable by usual analytical methods.

In one embodiment the mother's milk or the mother's milk fed to the infant is depleted in at least one fucosylated oligosaccharide(s) in the sense that it has a concentration of said fucosylated oligosaccharides, preferably said oligosaccharides comprising a 2' fucosyl-epitope, more preferably in said 2FL, of less than 3000 mg/L, less than 2000 mg/L, less than 1000_mg/l, less than 500 mg/L, less than 300 mg/L, less than 100 mg/L, less than 50 mg/L, less than 10 mg/L, 1 mg/L of said oligosaccharide, preferably said oligosaccharides comprising a 2'-fucosyl-epitope, more preferably in said 2FL.

In one embodiment the infant or young child is actually fed or partially fed, or temporarily fed with the mother's milk or mother's colostrum.

In one embodiment the composition of the invention is given to the infant or young child as a supplementary composition to the mother's milk or mother's colostrum. In one embodiment the composition is given to the infant or young child as the sole or primary nutritional composition during at least one period of time, e.g. after the $1^{st}$, $2^{nd}$ or $4^{th}$ month, during at least 1, 2, 4 or 6 months. Preferably the infant or young child receives the mother's milk and/or mother's colostrums during at least the first 2 weeks, first 1, 2, 4, or 6 months. In one embodiment the composition of the invention is given to the infant or young child after such period of mother's nutrition, or is given together with such period of mother's milk nutrition.

In particular embodiments the infant or young child is breastfed with a mother's milk from a non-secretor mother. Genetic variants of specific glycosyltransferases are well known to affect very specific milk prebiotic components and glycan structures. The basis for the phenotypic difference between the secretor and non-secretor subpopulations stems from genetic polymorphisms resulting in the expression of a specific functional alpha-1,2-fucosyltransferase (also called fucosyltransferase-2 or Fut2) in case of secretors whereas non-secretors do not express this functional alpha-1,2-fucosyltransferase. Accordingly, mutations in this gene lead to deficient amounts of 2' fucosyl-glycans (oligosaccharides) secreted into biological fluids (such as milk) of non-secretors people. The secretor (sec+ or sec$^+$) and non-secretor (sec− or sec$^-$) status of a person can be determined using the Lewis blood typing system, commonly known by a skilled man and also explained in WO2011136648. In one embodiment of the present invention the mother is a sec− mother.

WO2011136648A1 (Bernd Stahl, Nutricia NV) provides background on the use of particular oligosaccharides in infant nutrition especially for subjects characterized by their own or their mother's Lewis blood types. The document however fails to disclose specific health effects.

Sibling: The sibling can be a brother or a sister who can be younger or older than the infant. In some embodiments the infant has at least one sibling who is older than him i.e. the infant has at least one sibling at birth. It may especially be a child (including young child) who is very likely to bring allergens in the family environment, or is susceptible to infections (e.g. URT infections) since he/she comes into close contact with many other individuals, e.g., in school or in kinder garden.

The term "HMO" or "HMOs" refers to human milk oligosaccharide(s). These carbohydrates are highly resistant to enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

A "fucosylated oligosaccharide" is an oligosaccharide having a fucose residue. It has a neutral nature. Some examples are 2-FL (2'-fucosyllactose) (also abbreviated 2FL, 2'FL, or 2'-FL), 3-FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose, difucosyllacto-N-hexaose I, difucosyllacto-N-neohexaose II and any combination thereof. Without wishing to be bound by theory it is believed that the fucosyl-epitope of the fucosylated oligosaccharides may act as decoy at the mucosal surface. By a competition effect, it may prevent and/or limit the action of the pathogens responsible of infections (of viral or bacterial origin) or of their secreted components (e.g. toxins), especially by avoiding their binding to natural ligands, and this will therefore reduce the risk of infections, and particularly of URT infections.

The expressions "fucosylated oligosaccharide comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected. Without wishing to be bound by theory the 2'-fucosyl-epitope of these fucosylated oligosaccharides is believed to be particularly specific to pathogens (or their secreted components) involved in URT infections.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose) and LNnT (lacto-N-neotetraose).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995; 125:1401-12).

The term "probiotic" means microbial cell preparations or components of microbial cells with a beneficial effect on the health or well-being of the host. (Salminen S, Ouwehand A. Benno Y. et al. "*Probiotics: how should they be defined*" Trends Food Sci. Technol. 1999:10 107-10). The microbial cells are generally bacteria or yeasts.

The term "cfu" should be understood as colony-forming unit.

All percentages are by weight unless otherwise stated.

The invention will now be described in further details. It is noted that the various aspects, features, examples and embodiments described in the present application may be compatible and/or combined together.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

A first object of the present invention is therefore a composition comprising at least one fucosylated oligosaccharide, for use (or suitable for use) in preventing, reducing and/or treating allergies in an infant or young child born from a mother deficient in at least one fucosylated oligosaccharide(s), a sec⁻ mother, or fed with a mother's milk deficient in at least one fucosylated oligosaccharide(s).

It is hypothesized that such subjects would not be exposed and/or would not get the necessary amount of fucosylated oligosaccharide(s), especially 2-FL. Indeed the mother will not be able to pass to the subject such necessary quantity of fucosylated oligosaccharide(s). The right amount of necessary of fucosylated oligosaccharide(s), in particular 2FL is hypothesized to provide a protection against allergies.

In one embodiment the subject is born from a sec⁻ (sec–) mother which mother's milk is deficient or depleted in fucosylated oligosaccharide(s), especially 2FL. In one embodiment the subject is not fed with any human milk or is fed only during the first week, first 2, 4 weeks, first 2 or 4 months with milk deficient in at least one fucosylated oligosaccharide(s). In these instances the supplementation of the nutrition given to the subject with at least one fucosylated oligosaccharide(s) such as 2FL, will enhance the protection of the subject against allergies, or reduce his risk of allergies.

In one embodiment the infant or young child is fed, at least initially (during the first week or first 2 weeks, or first 1, 2, 4, or 6 months of life) with an infant formula that is low in, or depleted in, fucosylated oligosaccharide(s), especially 2FL.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or follow-on formula.

In one embodiment the nutritional composition of the invention is given to the subject (infant or young child) at birth. In one embodiment the nutritional composition of the invention is given to the subject after the human breast milk feeding is stopped, after the first, $2^{nd}$, $3^{rd}$, $4^{th}$, $6^{th}$ month of age. The feeding of the nutritional composition of the invention can last for 1, 2, 4, weeks or 1, 2, 4, 6 months or 1 or 2 years.

It is understood that a nutritional intervention with the nutritional composition of the invention is seen to be more efficient to provide the health benefit on allergy when started at birth or soon after birth and/or for a period of at least 4 or 6 weeks. Indeed it is hypothesized that such interventions are able to educate the immune system in order to best modulate the allergic pathways in the early days.

In one embodiment the subject receives human milk during an initial period of 1, 2, or 4 weeks, or 1, 2, 4 months starting just after birth or starting 1 week, 2 or 4 weeks after birth.

In one embodiment of the invention the nutritional composition comprises more than 0.05 g/100 g, more than 1 g more than 2 more than 5 g, more than 10 g of at least one fucosylated oligosaccharide(s), or of 2FL. In one embodiment the composition comprises between 0.05 and 10 g/100 g of composition, between 0.1 and 3 g, between 1 and 2 g of at least one fucosylated oligosaccharide(s), or of 2FL.

In some embodiments the infant or young child is fed with a mother's milk from a non-secretor mother (sec⁻ mother).

The infant or young child can be secretor or non-secretor using the Lewis blood typing system. In a particular embodiment, the infant or young child is secretor. This implies that the infant or young child will express some surface epitopes (analogues) for at least one fucosylated oligosaccharide(s), and especially for at least one fucosylated oligosaccharide comprising a 2'-fucosyl-epitope (also called 2-fucosylated oligosaccharides) such as 2FL.

In a particular embodiment, the infant or young child is secretor using the Lewis blood typing system whereas he was born from a non-secretor (=sec−) mother.

In a particular embodiment, the infant or young child is non-secretor using the Lewis blood typing system whereas he was born from a non-secretor (=sec−) mother.

It is understood that the effects of the composition of the invention are statistically more visible when provided to subjects, which are particularly at risk of allergies.

In one embodiment the composition is intended for infant or young child born by c-section or preterm infants. Indeed such infants or young child are more susceptible to be or become allergic. One can hypothesize that the immaturity of their immune system at birth or the lack of contact with the vaginal flora influences their tolerance development and allergy risk.

FIG. 1 actually shows that infants born from sec⁻ mothers by C-section have, at 2 years, a higher occurrence of allergic diseases.

Similarly, FIG. 2 shows that infants born from sec− mothers by C-section have a higher frequency of atopic diseases and eczema.

In one embodiment the composition of the invention is intended to infants born having siblings, especially when they have siblings at birth. Those infants are indeed more prone to allergies and are at greater risk of allergies.

In one embodiment the composition is intended to subjects having a family history of allergies or atopic diseases. They are hence particularly at risk of allergies and will benefit in a greater way from the composition of the invention.

In some other embodiments the infant combined multiple allergy risk, for example is born by C-section and has a family history of allergy or is born by C-section and has at least one sibling.

The composition of the present invention comprises at least one fucosylated oligosaccharide. There can be one or several fucosylated oligosaccharide(s). The fucosylated oligosaccharide(s) can be selected from the list comprising 2'-fucosyllactose(2-FL or 2FL), 3' fucosyllactose, difucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difucosyllacto-N-neohexaose I, difuco-lacto-N-neohexaose, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2' fucosyl-epitope. It can be for example selected from the list comprising 2'-fucosyllactose, difucosyllactose, lacto-N-fucopentaose, lacto-N-fucohexaose, lacto-N-difucohexaose, fucosyllacto-N-hexaose, fucosyl-lacto-N-neohexaose, difucosyllacto-N-hexaose difuco-lacto-N-neohexaose, difucosyllacto-N-neohexaose, fucosyl-para-Lacto-N-hexaose and any combination thereof.

Some examples of lacto-N-fucopentaose are lacto-N-fucopentaose I, lacto-N-fucopentaose II, lacto-N-fucopentaose III, lacto-N-fucopentaose V.

In a particular embodiment of the present invention the fucosylated oligosaccharide is 2'-fucosyllactose (2-FL).

The fucosylated oligosaccharide may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa Hakko Kogyo of Japan.

The composition according to the invention can contain from 0.1 to 10 g of fucosylated oligosaccharide(s) per 100 g of composition on a dry weight basis, e.g. from 0.1 to 8 g, or from 0.1 to 4 g, or from 0.5 to 3 g of fucosylated oligosaccharide(s) per 100 g of composition on a dry weight basis.

In particular examples the composition comprises from 0.5 to 10 g/L of fucosylated oligosaccharide(s), or from 0.5 to 5 g/L, or from 1 to 4.5 g/L, or from 2 to 4 g/L, or from 2.5 to 3.5 g/L of fucosylated oligosaccharide(s). The amount of fucosylated oligosaccharide(s) will be adapted depending on the needs of the infant. In some examples, the composition can comprise from 0.5 to 2 g/L or from 0.7 to 1.8 g/L of fucosylated oligosaccharide(s). In some other examples, the composition can comprise higher levels of fucosylated oligosaccharide(s) such as from 5 to 10 g/L or from 6 to 8 g/L of fucosylated oligosaccharide(s), especially 2FL.

The composition according to the invention can comprise at least another human milk oligosaccharide(s) and/or precursor(s) thereof. There can be one or several other human milk oligosaccharide(s) and/or precursor(s) thereof, for example 1, 2, 3, 4, 5 or even more HMO(s) (and/or precursor(s) thereof) other than the at least one fucosylated oligosaccharide(s).

These other human milk oligosaccharide(s) and/or precursor(s) thereof may be selected from the list comprising N-acetylated oligosaccharide, sialylated oligosaccharide, sialic acid, fucose and any combination thereof.

Therefore the composition according to the invention can also comprise N-acetylated oligosaccharide(s). There can be one or several N-acetylated oligosaccharide(s).

The N-acetylated oligosaccharide(s) can be selected from the group comprising lacto-N-tetraose (LNT), lacto-N-neotetraose (LNnT) and any combination thereof.

In some particular embodiments the N-acetylated oligosaccharide is LNT.

In some particular embodiments the N-acetylated oligosaccharide is LNnT.

In some particular embodiments the N-acetylated oligosaccharide is a mixture of LNT and LNnT.

In some particular embodiments the composition comprises both LNT and LNnT in a ratio LNT:LNnT between 5:1 and 1:2, or from 2:1 to 1:1, or from 2:1.2 to 2:1.6. In one embodiment the ratio of LNT/LNnT is less than 8, less than 6 or less than 4.

LNT and LNnT may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

The composition according to the invention can contain from 0.1 to 5 g of N-acetylated oligosaccharide(s)/100 g composition on a dry weight basis or from 0.1 to 3 g of N-acetylated oligosaccharide(s)/100 g composition on a dry weight basis.

In particular examples the composition comprises LNT in an amount of from 0.1 to 4, or from 0.3 to 3 or from 0.4 to 2 or from 0.4 to 1, or from 0.4 to 0.9 g/L of composition.

In particular examples the composition comprises LNnT in an amount of from 0.1 to 4, or from 0.2 to 2 or from 0.3 to 1.5 or from 0.4 to 1, or from 0.4 to 0.9 g/L of composition. In some embodiments, the composition comprises both LNT and LNnT in these above-mentioned concentrations.

The composition according to the invention can comprise sialylated oligosaccharide(s). There can be one or several sialylated oligosaccharide(s).

The sialylated oligosaccharide(s) can be selected from the group comprising 3' sialyllactose (3-SL), 6' sialyllactose (6-SL), and any combination thereof.

In some embodiments of the invention the composition comprises 3-SL and 6-SL.

In some particular embodiments the ratio between 3'-sialyllactose (3-SL) and 6'-sialyllactose (6-SL) can be in the range between 5:1 and 1:10, or from 3:1 and 1:1, or from 1:1 to 1:10.

In some specific embodiments the sialylated oligosaccharide of the composition is 6' sialyllactose (6-SL).

The 3'- and 6'-forms of sialyllactose may be isolated by chromatographic or filtration technology from a natural source such as animal milks. Alternatively, they may be produced by biotechnological means using specific sialyltransferases or sialidases, neuraminidases, by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

The composition according to the invention can contain from 0.05 to 5 g of sialylated oligosaccharide(s) per 100 g of composition on a dry weight basis, e.g from 0.1 to 2 g or to 3 g or from 0.2 to 1 g, or 0.3 to 3 g of sialylated oligosaccharide(s) per 100 g of composition on a dry weight basis.

In particular examples the composition comprises from 0.05 to 5 g/L of sialylated oligosaccharide(s), or from 0.1 to 4 g/L, or from 0.3 to 2 g/L, or from 0.4 to 1.5 g/L, or from 0.4 to 1 g/L, for example 0.5 or 0.9 g/L of sialylated oligosaccharide(s).

In some particular embodiments the composition can comprise from 0.8 to 1.7 g/l of sialylated oligosaccharide(s).

The composition according to the present invention may optionally also comprise at least one precursor of human milk oligosaccharide. There can be one or several precursor(s) of human milk oligosaccharide.

For example the precursor of human milk oligosaccharide is sialic acid, fucose or a mixture thereof.

In some particular embodiments the composition comprises sialic acid.

The composition according to the invention can contain from 0 to 2.3 g of precursor(s) of human milk oligosaccharide per 100 g of composition on a dry weight basis, e.g from 0 to 1.5 g or from 0 to 0.8 g of precursor(s) of human milk oligosaccharide per 100 g of composition on a dry weight basis.

In particular examples the composition comprises from 0 to 3 g/L of precursor(s) of human milk oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of human milk oligosaccharide.

In some particular embodiments the composition of the present invention therefore comprises at least one fucosylated oligosaccharide in combination with at least another human milk oligosaccharide(s) and/or precursor(s) thereof selected from the list comprising lacto-N-tetraose (LNT), lacto-N-neotetraose (LNnT), 3' sialyllactose (3-SL), 6' sialyllactose (6-SL), sialic acid and any combination thereof.

Probiotics:

The composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonfi* CNCM 1-1225, *Streptococcus salivarius* DSM 13084 sold by BLIS Technologies Limited of New Zealand under the designation KI2, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The composition according to the invention typically contains from 10e3 to 10e12 cfu of probiotic strain, more preferably between 10e7 and 10e12 cfu or between 10e8 and 10e10 cfu of probiotic strain per g of composition on a dry weight basis.

In one embodiment the probiotics are viable. In another embodiment the probiotics are or comprise non replicating or inactivated probiotics.

The composition of the invention can further comprise at least one non-digestible oligosaccharide (e.g. prebiotics) other than the human milk oligosaccharides previously mentioned. They are usually in an amount between 0.3 and 10% by weight of composition.

Prebiotics:

Prebiotics are usually non-digestible in the sense that they are not broken down and absorbed in the stomach or small intestine and thus remain intact when they pass into the colon where they are selectively fermented by the beneficial bacteria. Examples of prebiotics include certain oligosaccharides, such a fructooligosaccharides (FOS) and galactooligosaccharides (GOS). A combination of prebiotics may be used such as 90% GOS with 10% short chain fructooligosaccharides such as in the product by BENEO-Orafti sold under the trademark Orafti® oligofructose (previously Raftilose®) or 10% inulin such as in the product sold by BENEO-Orafti under the trademark Orafti® inulin (previously Raftiline®). A particularly preferred combination of prebiotics is 70% short chain fructo-oligosaccharides and 30% inulin, which is a product sold by BENEO-Orafti under the trademark "Prebio 1".

The composition of the invention can further comprise at least one phage (bacteriophage) or a mixture of phages, preferably directed against pathogenic Streptococci, *Haemophilus, Moraxella* and Staphylococci.

The composition according to the invention can be a nutritional composition, a preparation or a food product.

The composition according to the invention can be for example a nutritional composition such as a synthetic nutritional composition. It can be an infant formula, a starter infant formula, a follow-on formula, a baby food, an infant cereal composition, a fortifier such as a human milk fortifier, or a supplement. Preferably the composition of the invention is an infant formula, or a fortifier or a supplement intended for the first 4 or 6 months of age.

In some other embodiments the composition of the present invention is a fortifier.

The fortifier can be a breast milk fortifier or formula fortifier such as an infant formula fortifier. The fortifier is therefore a particularly advantageous embodiment when the infant or young child is fed with a mother's milk deficient in at least one fucosylated oligosaccharide(s), e.g. a breast mother's milk from a non-secretor mother. Indeed, in an advantageous embodiment, the composition is a human milk fortifier especially designed for non-secretor mothers or other mothers whose milk has low amounts of at least one fucosylated oligosaccharide(s) such as 2'-fucosylated oligosaccharide(s).

When the composition is a supplement, it can be provided in the form of unit doses.

The composition according to the invention can be used in infants at risk that are term or preterm infants.

In a particular embodiment the composition of the invention is for use in infants or young child at risk that are also preterm infants.

In some embodiments the composition according to the invention can be for use before and/or during the weaning period.

When there are several oligosaccharide(s) (i.e. either several fucosylated oligosaccharides or one fucosylated oligosaccharide with at least another human milk oligosaccharide(s) and/or the precursor(s) thereof), they may be administered in the same composition or they may be administered sequentially.

The composition of the present invention can be in solid (e.g. powder), liquid or gelatinous form.

For example, when the infant at risk is an infant born by C-section, the composition could advantageously be a nutritional composition consumed in liquid form. In this case it may be a nutritionally complete formula such as an infant formula, a starter formula, a follow-on formula or a fortifier such as a human milk fortifier.

Proteins:

In one embodiment the composition of the invention comprises a source of protein. Such protein source can deliver between 1.6 and 3 g protein/100 kcal. In one embodiment intended for premature infants, such amount can be between 2.4 and 4 g/100 kcal or more than 3.6 g/100 kcal. In one embodiment the amount can be below 2.0 g per 100 kcal, e.g. in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

Preferably the protein source is whey predominant (more than 50% of proteins are coming from whey proteins). In one embodiment the protein of the composition are intact proteins or mostly (more than 90%) intact proteins.

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20%), for example for infants believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In one preferable embodiment the proteins of the composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80, 90. It is understood that hydrolyzed proteins can have several effects on allergy: hydrolyzed proteins can be less allergenic, hence triggering less immune allergic reactions. Hydrolyzed proteins, especially small peptides (of less than 20, 10 or 5 amino acids), can induce oral tolerance hence influencing the future allergic status of the subject. It is understood that hydrolyzed proteins can advantageously combine with the fucosylated oligosaccharide(s) of the present invention by providing a dual effect, possibly synergistic effect by acting at least at 2 different levels in the establishment of allergic symptoms or allergic status.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one embodiment the hydrolyzed proteins is the sole source of protein (i.e. 100% or at least 90% of protein are hydrolyzed).

In one embodiment the hydrolyzed proteins is the primary source of protein (i.e. at least 50%, preferably 60% of proteins are hydrolyzed).

In a particular embodiment the composition according to the invention is a hypoallergenic composition. In another particular embodiment the composition according to the invention is a hypoallergenic nutritional composition.

Carbohydrates:

The composition according to the present invention generally contains a carbohydrate source. This is particularly preferable in the case where the nutritional composition of the invention is an infant formula. In this case, any carbohydrate source conventionally found in infant formulae such as lactose, sucrose, maltodextrin, starch and mixtures thereof may be used although one of the preferred sources of carbohydrates is lactose.

Lipids:

The composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n–6 to n–3 fatty acids of about 5:1 to about 15:1; for example about 8:1 to about 10:1.

Minerals and Vitamins:

The composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the composition of the invention may contain emulsifiers and stabilisers such as soy, lecithin, citric acid esters of mono- and di-glycerides, and the like.

The composition of the invention may also contain other substances which may have a beneficial effect such as lactoferrin, nucleotides, nucleosides, and the like.

The composition according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The fucosylated oligosaccharide(s) (and the optional other human milk oligosaccharide(s) and/or the precursor(s) thereof) may be added at this stage, especially if the final product is to have a liquid form.

If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The fucosylated oligosaccharide(s) (and the optional other human milk oligosaccharide(s) and/or the precursor(s) thereof) may be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement including fucosylated oligosaccharide(s) (and the optional other human milk oligosaccharide(s) and/or the precursor(s) thereof) in an amount sufficient to achieve the desired effect in an individual.

The daily dose of the fucosylated oligosaccharide(s) is typically from 0.1 to 4 g, the daily dose of N-acetylated oligosaccharide(s) is typically from 0.1 to 3 g, the daily dose of the sialylated oligosaccharide(s) is typically from 0.1 to 2 g.

The amount of oligosaccharides to be included in the supplement will be selected according to the manner in which the supplement is to be administered. For example, if the supplement is to be administered twice a day, each supplement may contain from 0.05 to 1.5 g of N-acetylated oligosaccharide(s), from 0.05 to 1 g of sialylated oligosaccharide(s), and from 0.05 to 2 g of fucosylated oligosaccharide(s).

The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The composition can be administered (or given) at an age and for a period that depends on the needs. The composition is for use in preventing and/or treating URT infections.

The composition can be given immediately after birth of the infants at risk. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some other embodiments, the composition of the invention is given few days, or few weeks, or few months after birth. This may be especially the case when the infant at risk is premature, but not necessarily.

The composition of the invention can be given for some days (1, 2, 3, 4, 5, 6 . . . ), or for some weeks (1, 2, 3, 4, 5, 6, 7, 8 or even more), or for some months (1, 2, 3, 4, 5, 6, 7, 8, 9, 10, 11 or even more), depending on the needs.

Another object of the present invention is the use of at least one fucosylated oligosaccharide in the preparation of a composition to be administered for use in preventing allergies and/or treating allergies and/or reducing the occurrence or the risk of allergies in an infant or a young child born from a mother deficient in at least one fucosylated oligosaccharide(s) or fed with a mother's milk deficient in at least one fucosylated oligosaccharide(s)

The present invention also relates to a method for preventing allergies and/or treating allergies and/or reducing the occurrence or the risk of allergies in an infant or a young child born from a mother deficient in at least one fucosylated oligosaccharide(s) or fed with a mother's milk deficient in at least one fucosylated oligosaccharide(s). Said method comprises administering to said infant or young child a composition comprising at least one fucosylated oligosaccharide.

The different embodiments, details and examples previously described in the specification can similarly be applied to these uses and methods.

EXAMPLES

The following examples illustrate some specific embodiments of the composition for use according to the present invention. The examples are given solely for the purpose of illustration and are not to be construed as limitations of the present invention, as many variations thereof are possible without departing from the spirit of the invention.

Example 1

An example of the composition of an infant formula according to the present invention is given in the below table 1. This composition is given by way of illustration only.

TABLE 1 an example of the composition of an infant formula according to the present invention

| Nutrient | per 100 kcal | per liter |
|---|---|---|
| Energy (kcal) | 100 | 670 |
| Protein (g) | 1.83 | 12.3 |
| Fat (g) | 5.3 | 35.7 |
| Linoleic acid (g) | 0.79 | 5.3 |
| α-Linolenic acid (mg) | 101 | 675 |
| Lactose (g) | 11.2 | 74.7 |
| Minerals (g) | 0.37 | 2.5 |
| Na (mg) | 23 | 150 |
| K (mg) | 89 | 590 |
| Cl (mg) | 64 | 430 |
| Ca (mg) | 62 | 410 |
| P (mg) | 31 | 210 |
| Mg (mg) | 7 | 50 |
| Mn (μg) | 8 | 50 |

TABLE 1-continued an example of the composition of an infant formula
according to the present invention

| Nutrient | per 100 kcal | per liter |
|---|---|---|
| Se (µg) | 2 | 13 |
| Vitamin A (µg RE) | 105 | 700 |
| Vitamin D (µg) | 1.5 | 10 |
| Vitamin E (mg TE) | 0.8 | 5.4 |
| Vitamin K1 (µg) | 8 | 54 |
| Vitamin C (mg) | 10 | 67 |
| Vitamin B1 (mg) | 0.07 | 0.47 |
| Vitamin B2 (mg) | 0.15 | 1.0 |
| Niacin (mg) | 1 | 6.7 |
| Vitamin B6 (mg) | 0.075 | 0.50 |
| Folic acid (µg) | 9 | 60 |
| Pantothenic acid (mg) | 0.45 | 3 |
| Vitamin B12 (µg) | 0.3 | 2 |
| Biotin (µg) | 2.2 | 15 |
| Choline (mg) | 10 | 67 |
| Fe (mg) | 1.2 | 8 |
| I (µg) | 15 | 100 |
| Cu (mg) | 0.06 | 0.4 |
| Zn (mg) | 0.75 | 5 |
| 2FL (g) | 0.45 | 3 |

Example 2

The amounts of the oligosaccharides 2FL (2' fucosyllactose) of human milk samples from a cohort of mother-infant pairs were analyzed. These data were correlated to the number of respiratory infections from 0-2 years of age among the infants. In the cohort of 266 infants, 33 infants consumed milk deficient in 2FL and 233 infants consumed milk with 2FL. 147 infants had no siblings at birth and 119 infants had at least one sibling at birth. 51 infants were born by C-section and 215 infants were born by vaginal birth.

Briefly, milk samples were homogenized and diluted in water, generally 1/10 and 1/100. Diluted samples were centrifuged to remove particles and supernatants were analyzed by high performance anion exchange chromatography coupled with a pulsed amperometric detector (HPAEC-PAD, ICS3000, Dionex) using a Carbopac PA1 analytical column for separation of individual oligosaccharides. Quantification was done with authentic oligosaccharide external standard curves. Peak identification was based on co-migration with authentic oligosaccharide standards.

We performed statistical analyses to find possible associations between (i) the milk types (presence or absence of 2FL or other oligosaccharides) that the infants of the cohort consumed and (ii) the occurrence of allergic diseases at age 2 and 5.

FIGS. 1 and 2 shows that infants having consumed milk from sec⁻ (non secretor) mothers and born by C-section had a higher frequency of occurrence of allergic diseases, in particular at the age of 2, in particular eczema and atopic diseases. This reinforces the concept of the invention highlighting the high needs of these infants who are particularly at risk of allergies. The beneficial effect of providing these infants with supplementary 2-fucosylated oligosaccharide (e.g. 2FL) will therefore be more prominent in these infants.

FIG. 3 shows that the level of 2FL varies greatly in various human breast milk form various mothers. It shows a correlation between the amount of 2FL in the human breast milk fed to the infants during the first months of life and the risk of allergies (occurrence of Eczema and atopic diseases at 2 years). This demonstrates that the sec⁻ status of a mother is not the only factor predictive of allergy risk but also that the amount of fucosylated oligosaccharide in the human breast milk is another factor. The lower the level of fucosylated oligosaccharide (e.g. 2FL) in the human breast milk fed to the infants in the first months of life, the higher the risk of allergy is (especially atopic diseases such as atopic dermatitis or eczema).

FIG. 4 shows that other oligosaccharides in human breast milk can influence the allergic status of infants. The same infants as in FIG. 3 who developed allergies also had consumed a human mother's milk of higher LNT/LNnT ratio compared to those not developing allergies.

A composition comprising at least one fucosylated oligosaccharide, preferably 2FL, will therefore be efficient for use in treating allergies and/or reducing the occurrence or risk of allergies in infants or young child, especially in those infants who are at risk.

The invention claimed is:

1. A method for treating allergies and/or reducing the occurrence or a risk of allergies in an infant or young child born by caesarean section (C-section) and fed with a mother's milk having an amount of 2'-fucosylated oligosaccharides that is less than 3,000 mg/L, the method comprising administering to the infant or young child a composition comprising an effective amount of 2'-fucosyllactose (2FL) that is the only human milk oligosaccharide in the composition.

2. The method according to claim 1 wherein the infant or young child has at least one sibling and/or has a family history of allergy.

3. The method according to claim 1 wherein the effective amount of the 2FL is effective to treat and/or reduce a risk of allergies that start to occur at or before the age of 2 and/or comprises eczema or atopic diseases.

4. The method according to claim 1 wherein the composition comprises 0.1 g to 10 g of the 2FL per 100 g of the composition on a dry weight basis.

5. The method according to claim 1 wherein the composition comprises 1 g to 2 g of the 2FL per 100 g of the composition on a dry weight basis.

6. The method according to claim 1, wherein the composition further comprises at least one probiotic in an amount of from $10^3$ to $10^{12}$ cfu/g of the composition (dry weight).

7. The method according to claim 1, wherein the composition is selected from the group consisting of a nutritional composition, a preparation and a food product.

8. The method according to claim 1, wherein the composition is selected from the group consisting of an infant formula, a starter infant formula, a follow-on infant formula, a baby food, an infant cereal composition, a fortifier, a human milk fortifier and a supplement.

9. The method according to claim 1, wherein the infant is born preterm.

10. The method according to claim 1, wherein the composition comprises hydrolyzed proteins as sole source or primary source of proteins.

11. The method according to claim 1, wherein the infant or young child is secretor.

* * * * *